(12) United States Patent
Denton et al.

(10) Patent No.: US 7,601,540 B2
(45) Date of Patent: Oct. 13, 2009

(54) GAMMA SECRETASE NOTCH BIOMARKERS

(75) Inventors: Rex Denton, Madison, CT (US); Jere E. Meredith, Haddam, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 75 days.

(21) Appl. No.: 11/779,306

(22) Filed: Jul. 18, 2007

(65) Prior Publication Data

US 2008/0020395 A1   Jan. 24, 2008

Related U.S. Application Data

(60) Provisional application No. 60/831,608, filed on Jul. 18, 2006.

(51) Int. Cl.
*G01N 33/483* (2006.01)
*G01N 33/50* (2006.01)
*G01N 33/53* (2006.01)
*C07K 14/435* (2006.01)
*A61K 38/00* (2006.01)

(52) U.S. Cl. .......................... 436/63; 436/86; 436/501; 435/7.1; 435/7.92; 514/2; 530/350

(58) Field of Classification Search .................. None
See application file for complete search history.

(56) References Cited

FOREIGN PATENT DOCUMENTS

WO   WO97/33551      9/1997
WO   WO-2005013802 A2 *  2/2005

OTHER PUBLICATIONS

Thim, L. Trefoil peptides: from structure and function. Cell Mol Life Sci 53: 888-903, 1997.*
Barten et al. Gamma secretase inhibitors for Alzheimer's Disease. Drugs R D 7(2): 87-97, 2006.*
Nozaki et al. Regulation and function of trefoil factor family 3 expression in the biliary tree. Am J Pathol 165(6): 1907-1920, 2004.*
Washizawa et al. Comparative effects of glucagon-like peptide-2 (GLP-2), Growth Hormone (GH), and keratinocyte growth factor (KGF) on markers of gut adaptation after massive small bowel resection in rats. JPEN 28(6): 399-409, 2004.*
Blanchard et al. IL-4 and IL-13 up-regulate intestinal trefoil factor expression: requirement for STAT6 and de novo protein synthesis. J Immunol 172(6): 3775-3783, 2004.*
Xian et al. Temporal changes in TFF3 expression and jejunal morphology during methotrexate-induced damage and repair. Am J Physiol 277: G785-G795, 1999.*
Durual et al. Expression of human TFF3 in relation to growth of HT-29 cell subpopulations: involvement of PI3-K but not STAT6. Differentiation 73: 36-44, 2005.*
Artavanis-Tsakonas, S. et al., "Notch Signaling: Cell Fate Control and Signal Integration in Development", Science, vol. 284, pp. 770-776 (1999).
Ausubel, F., Short Protocols in Molecular Biology, Fifth Edition, Wiley publishers (2002).

Barten, D. et al., "Dynamics of β-Amyloid Reductions in Brain, Cerebrospinal Fluid, and Plasma of β-Amyloid Precursor Protein Transgenic Mice Treated with a γ-Secretase Inhibitor", The J. of Pharmacology and Experimental Therapeutics, vol. 312(2), pp. 635-643 (2005).
Brou, C. et al., "A Novel Proteolytic Cleavage Involved in Notch Signaling: The Role of the Disintegrin-Metalloprotease TACE", Molecular Cell, vol. 5, pp. 207-216 (2000).
De Strooper, B. et al., "A presenilin-1-dependent γ-secretase-like protease mediates release of Notch intracellular domain", Nature, vol. 398, pp. 518-522 (1999).
De Strooper, B., "Aph-1, Pen-2, and Nicastrin with Presenilin Generate an Active γ-Secretase Complex", Neuron, vol. 38, pp. 9-12 (2003).
Donoviel, D. et al., "Mice lacking both presenilin genes exhibitearlyembryonic patterning defects", Genes & Development, vol. 13, pp. 2801-2810 (1999).
Hardy, J. et al., "The Amyloid Hypothesis of Alzheimer's Disease: Progress and Problems on the Road to Therapeutics", Science, vol. 297, pp. 353-357 (2002).
Herreman, A, et al., "Presenilin 2 deficiency causes a mold pulmonary phenotype and no changes in amyloid precursor protein processing but enhances the embryonic lethal phenotype of presenilin 1 deficiency", PNAS, vol. 96(21), pp. 11872-11877 (1999).
Huppert, S. et al., "Embryonic lethality in mice homozygous for a processing-deficient allele of Notch 1", Nature, vol. 405, pp. 966-970 (2000).
Jarriault, S. et al., "Delta-1 Activation of Notch-1 Signaling Results in *HES-1* Transactivation", Molecular and Cellular Biology, vol. 18(12), pp. 7423-7431 (1998).
Jensen, J. et al., "Control of endodermal endocrine development by Hes-1", Nature Genetics, vol. 24, pp. 36-44 (2000).
Kadesch, T., "Review: Notch Signaling: A Dance of Proteins Changing Partners", Experimental Cell Research, vol. 260, pp. 1-8 (2000).
Kopan, R. et al., "Signal transduction by activated mNotch: Importance of proteolytic processing and its regulation by the extracellular domain", PNAS, vol. 93, pp. 1683-1688 (1996).
Levitan, D. et al., "Effects of SEL-12 presenilin on LIN-12 localization and function in *Caenorhabditis elegans*", Development vol. 125(18), pp. 3599-3606 (1998).
Levitan, D. et al., "Facilitation of *lin-12*-mediated signaling by *sel-12*, a *Caenorhabditis elegans S182* Alzheimer's disease gene", Nature, vol. 377, pp. 351-354 (1995).

(Continued)

*Primary Examiner*—Bridget E Bunner
(74) *Attorney, Agent, or Firm*—Melissa Handler; Paul D. Golian

(57) ABSTRACT

The present invention relates to the biomarker TFF-3 that measures γ-secretase mediated Notch processing. TFF-3 has utility in predicting and/or determining in vivo Notch-related toxicity associated with inhibition of Notch processing mediated by γ-secretase. The reagents and methods of the invention can be utilized before, after, or concurrently with, pre-clinical, clinical, and/or post-clinical testing. The reagents and methods of the invention can be used to identify and maintain preferred doses of test compounds and thereby prevent medical complications, such as gastrointestinal cellular damage.

7 Claims, 2 Drawing Sheets

OTHER PUBLICATIONS

Logeat, F. et al., "The Notch1 receptor is cleaved constitutively by a furin-like convertase", PNAS, vol. 95, pp. 8108-8112 (1998).

Mattson, M., "Pathways towards and away from Alzheimer's disease", Nature, vol. 430, pp. 631-639 (2004).

Mizutani. T. et al., "Conservation of the biochemical mechanisms of signal transduction among mammalian Notch family members", PNAS, vol. 98(16), pp. 9026-9031 (2001).

Milano, J. et al., "Modulation of Notch Processing by γ-Secretase Inhibitors Causes intestinal Goblet Cell Metaplasia and Induction of Genes Known to Specify Gut Secretory Lineage Differentiation", Toxicological Sciences, vol. 82, pp. 341-358 (2004).

Mumm, J. et al., "A Ligand-Induced Extracellular Cleavage Regulates γ-Secretase-like Proteolytic Activation of Notch1", Molecular Cell, vol. 5, pp. 197-206 (2000).

Oddo, S. et al., "Triple-Transgenic Model of Alzheimer's Disease with Plaques and Tangles: Intracellular Aβ and Synaptic Dysfunction", Neuron, vol. 39, pp. 409-421 (2003).

Oddo, S. et al., "Aβ Immunotherapy Leads to Clearance of Early, but Not Late, Hyperphosphorylated Tau Aggregates via the Proteasome", Neuron, vol. 43, pp. 321-332 (2004).

Oddo, S. et al., "Amyloid deposition precedes tangle formation in a triple transgenic model of Alzheimer's disease", Neurobiology of Aging, vol. 24, pp. 1063-1070 (2003).

Ohtsuka, T. et al., "*Hes1* and *Hes5* as Notch effectors in mammalian neuronal differentiation", The EMBO Journal, vol. 18(8), pp. 2196-2207 (1999).

Pan, D. et al., "Kuzbanian Controls Proteolytic Processing of Notch and Mediates Lateral Inhibition during Drosophila and Vertebrate Neurogenesis", Cell, vol. 90, pp. 271-280 (1997).

Saxena, M. et al., "Murine Notch Homologs (N1-4) Undergo Presenilin-dependent Proteolysis", The J. of Biological Chemistry, vol. 276(43), pp. 40268-40273 (2001).

Petit, A. et al., "JLK Isocoumarin Inhibitors: Selective γ-Secretase Inhibitors That Do Not Interfere With Notch Pathway In Vitro or In Vivo", Journal of Neuroscience Research, vol. 74, pp. 370-377 (2003).

Sambrook, J. et al., Molecular Cloning- A Laboratory Manual, Third Edition, Cold Spring Harbor Laboratory Press (2001).

Schroeter, E. et al., "Notch-1 signalling requires ligand-induced proteolytic release of intracellular domain", Nature, vol. 393, pp. 382-386 (1998).

Searfoss, G. et al., "Adipsin, a Biomarker of Gastrointestinal Toxicity Mediated by a Functional γ-Secretase inhibitor", The J. of Biological Chemistry, vol. 278(46), pp. 46107-46116 (2003).

Struhl, G. et al., "Requirements for Presenilin-Dependent Cleavage of Notch and Other ransmembrane Proteins", Molecular Cell, vol. 6, pp. 625-636 (2000).

Struhl, G. et al., "Presenilin is required for activity and nuclear access of Notch in *Drosophila*", Nature, vol. 398, pp. 522-525 (1999).

Walsh, D. et al., "Deciphering the Molecular Basis of Memory Failure in Alzheimer's Disease", Neuron, vol. 44, pp. 181-193 (2004).

Weggen, S. et al., "A subset of NSAIDs lower amyloidogenic Aβ42 independently of cyclooxygenase activity", Nature, vol. 414, pp. 212-216 (2001).

Wong, G. et al., "Chronic Treatment with the γ-Secretase Inhibitor LY-411,575 Inhibits β-Amyloid Peptide Production and Alters Lymphopoiesis and Intestinal Cell Differentiation", The J. of Biological Chemistry, vol. 279(13), pp. 12876-12882 (2004).

Ye, Y. et al., "Neurogenic phenotypes and altered Notch processisng in *Drosophila presenilin* mutants", Nature, vol. 398, pp. 525-529 (1999).

Familari, M. et al., "Trefoil peptides are early markers of gastrointestinal maturation in the rat", Int. J. Dev. Biol., vol. 42, pp. 783-789 (1998).

Podolsky, D. et al., "Identification of Human Intestinal Trefoil Factor", The Journal of Biological Chemistry, vol. 268(9), pp. 6694-6702 (1993).

Schonhoff, S. et al., "Minireview: Development and Differentiation of Gut Endocrine Cells", Endocrinology, vol. 145(6), pp. 2639-2644 (2004).

Shroyer, N. et al., "*Gfi1* functions downstream of *Math1* to control intestinal secretory cell subtype allocation and differentiation", Genes & Development, vol. 19, pp. 2412-2417 (2005).

* cited by examiner

GAMMA SECRETASE NOTCH BIOMARKERS

This application claims priority from U.S. Provisional Application Ser. No. 60/831,608, filed Jul. 18, 2006, incorporated in its entirety herein by reference.

FIELD OF THE INVENTION

The present invention relates generally to gamma secretase (γ-secretase) and to biomarkers. More specifically, the invention relates to methods for measuring γ-secretase-mediated Notch processing in vivo by measuring changes in the expression of the biomarker Trefoil factor-3 (TFF-3). Said changes in TFF-3 expression correlate with Notch-related toxicity in the intestines associated with the modulation of γ-secretase-mediated activity. The invention also relates to employing TFF-3 expression to identify a preferred dose of a test compound and to the generation of a dosing schedule, which can be employed as part of a therapeutic regimen.

BACKGROUND OF THE INVENTION

Alzheimer's disease (AD) is a neurodegenerative disorder and the most common form of dementia in the elderly (reviewed in Hardy & Selkoe, (2002) *Science* 297(5580):353-6; Mattson, (2004) *Nature* 430(7000):631-9 and Walsh & Selkoe, (2004) *Neuron* 44(1):181-93). AD is characterized clinically by a progressive loss in cognitive function, including memory impairment, deterioration in language and visuospatial functions, and alterations in personality and behavior. Pathologically, AD is characterized by the presence of β-amyloid plaques and neurofibrillary tangles in the cortex and hippocampus. Amyloid β peptide (Aβ) is the main component of plaques and tau is the main component of tangles. Genetic evidence from familial early onset forms of AD (FAD) suggests that aggregation and accumulation of Aβ, specifically Aβ1-42, initiates the cascade of events leading to neuropathology and dementia. Further support for the amyloid hypothesis is provided by transgenic mouse models where overproduction of Aβ 1-42 recapitulates many of the hallmarks of AD including formation of plaques and cognitive deficits. Recent evidence from a triple transgenic mouse model of AD suggests that Aβ aggregation and accumulation proceeds and initiates tangle formation (Oddo et al., (2003) *Neurobiol. Aging* 24(8):1063-70; Oddo et al.,(2004) *Neuron* 43(3):321-32; Oddo et al., (2003) *Neuron* 39(3):409-21).

Aβ is generated by proteolytic processing of APP by two enzymes, β-amyloid cleavage enzyme (BACE) and gamma secretase (γ-secretase). γ-secretase is a complex comprised of four proteins: presenilin (presenilin-1 or -2), nicastrin APH-1 and PEN-2 (De Strooper, (2003) *Neuron* 38(1):9-12). Presenilin-1 and -2 contain transmembrane aspartyl residues that have been shown to be essential for catalytic processing activity of the complex. The majority of the mutations linked to the early onset, familial form of AD (FAD) are associated with either PS-1 or PS-2. γ-secretase appears to have the capacity to process any type I transmembrane protein that has undergone ectodomain shedding (Struhl & Adachi, (2000) *Mol. Cell* 6:625-636). In addition to APP, γ-secretase also been shown to cleave a number of other substrates including the Notch family of receptors (1-4), the Notch ligands Delta-1 and Jagged-2, E-Cadherin, ErbB4 and CD44 (De Strooper, (2003) *Neuron* 38(1):9-12). Genetic evidence indicates that the γ-secretase complex is critically required for Notch signaling and function, at least in the context of the developing embryo (Struhl & Greenwald, (1999) *Nature* (London) 398 (6727):522-525; Ye et al., (1999) *Nature* (London) 398(6727):525-529; Levitan & Greenwald, (1995) *Nature* (London) 377(6547):351-5; Levitan & Greenwald, (1998) *Development* (Cambridge, U. K.) 125(18):3599-3606; Huppert et al., (2000) *Nature* 405:966-970; Donoviel et al., (1999) *Genes Dev.* 13(21):2801-2810; Herreman et al., (1999) *Proc. Natl. Acad. Sci. U.S.A.* 96(21):11872-11877). The physiological role of γ-secretase-mediated cleavage of Notch in the adult and of the other substrates is not known.

Notch is an evolutionarily conserved and widely expressed single-span type I transmembrane receptor that plays a prominent role in regulating cell fate decisions in the developing embryo (reviewed in Artavanis-Tsakonas et al., (1999) *Science* 284(5415):770-6 and Kadesch, (2000) *Exp. Cell Res.* 260(1):1-8.). The role of Notch in the adult is less clear but Notch proteins are expressed in various adult tissues and are thought to play a role in regulating stem cell differentiation. Four Notch genes have been identified in mammals (Notch 1-4); all four Notch proteins are cleaved by γ-secretase (Mizutani et al., (2001) *Proc. Natl. Acad. Sci. U.S.A.* 98(16): 9026-9031). Notch activation is induced by binding, in trans, to the Delta/Serrate/LAG2 family of transmembrane ligands. Notch signal transduction is mediated by three cleavage events: (a) cleavage at Site 1 in the extracellular domain (Logeat et al., (1998) *Proc. Natl. Acad. Sci. U.S.A.* 95(14): 8108-12); (b) cleavage at Site 2 just N-terminal to the extracellular/transmembrane domain boundary following ligand binding (Brou et al., (2000) *Mol. Cell* 5(2):207-216; Mumm et al., (2000) *Mol. Cell* 5(2):197-206; Pan & Rubin, (1997) *Cell* 90(2):271-80); and (c) cleavage at Site 3 (S3) within the transmembrane near the transmembrane/cytoplasmic domain boundary (Schroeter et al., (1998) *Nature* (London) 393(6683):382-386; Kopan et al., (1996) *Proc. Natl. Acad. Sci. U.S.A.* 93(4):1683-8). Site 3 cleavage is required for release of the Notch intracellular domain (NICD) and is mediated by γ-secretase (Struhl & Greenwald, (1999) *Nature* (London), 398(6727):522-525; Levitan & Greenwald, (1998) *Development* (Cambridge, U. K.) 125(18):3599-3606; Mizutani et al., (2001) *Proc. Natl. Acad. Sci. U.S.A.* 98(16): 9026-9031; Saxena et al., (2001) *J. Biol. Chem.* 276(43): 40268-73; De Strooper et al., (1999) *Nature* (London) 398 (6727):518-522). NICD activates transcription mediated by the CBF1/Su(H)/LAG-1 family of DNA-binding proteins and induces expression of various genes including HES-1 (Jarriault et al., (1998) *Mol. Cell Biol.* 18(12):7423-31; Ohtsuka et al., (1999) *EMBO J.* 18(8):2196-207). NICD-regulated transcription is thought to be a key component of Notch-mediated signal transduction.

The development of γ-secretase inhibitors to block APP cleavage and Aβ generation is one therapeutic approach for the treatment of AD. This approach, however, is beset by the potential for mechanism-based toxicity due to inhibition of Notch processing. Indeed, Notch-related toxicities have been observed in studies where animals have been dosed subchronically with γ-secretase inhibitors (Wong et al., (2004) *J. Biol. Chem.* 279(13):12876-82; Searfoss et al., (2003) *J. Biol. Chem.* 278(46):46107-16; Milano et al., (2004) *Toxicol. Sci.* 82(1):341-58). One toxicity consistently observed following three or more days of treatment is an intestinal goblet cell metaplasia (Wong et al., (2004) *J. Biol. Chem.* 279(13):12876-82; Searfoss et al., (2003) *J. Biol. Chem.* 278 (46):46107-16; Milano et al., (2004) *Toxicol. Sci.* 82(1):341-58). This lesion is similar to the phenotype observed in Hes-1 KO mice (Jensen et al., (2000) *Nature Genet.* 24(1):36-44), suggesting that the inhibitor-induced lesion is linked to inhibition of Notch signaling through Hes-1. Another molecule mediated by Notch is Trefoil factor-3 (TFF-3), also known as Intestinal Trefoil factor (ITF). TFF-3 is abundantly expressed by goblet cells in the duodenum demonstrates remarkable resistance to both proteolytic and thermal degradation. In addition to the GI lesion, alterations in lymphocyte development have also been noted after 5-15 days of dosing, including thymus atrophy, reductions in thymocyte numbers and alterations in thymocyte differentiation. These results are also consistent with inhibition of Notch processing and inhibition of it's role in regulating lymphocyte development (Wong et al., (2004) *J. Biol. Chem.* 279(13):12876-82).

Despite the potential for mechanism-based toxicity, γ-secretase inhibitors have been developed with some or complete specificity for inhibiting APP processing (Petit et al., (2003) *J. Neurosci. Res.* 74(3):370-7; Weggen et al., (2001) *Nature* 414(6860):212-6; Barten et al., (2005) *J. Pharmacol. Exp. Ther.* 312(2):635-43). In order to screen such inhibitors in vivo, it is desirable that biomarkers be developed that can be employed to monitor safety with respect to potential Notch-related toxicities.

A set of indicators that could be used to gauge toxic effects in vivo would therefore be of great value. A single set of reagents and standards could be used to evaluate test compounds from initial screening, through testing in pre-clinical (e.g., drug discovery) species, and potentially in clinical trials. Such universal indicators of toxicity preferably meet several criteria. First, they preferably are able to correctly identify toxic compounds with diverse mechanisms of action, including various chemical classes/chemotypes. Second, changes in these biomarkers are preferably consistent, quantifiable and reflect the degree of toxic insult. Third, assays are generally adaptable to high throughput technologies without becoming prohibitively expensive. Fourth, in vivo sample collection is preferably non- or minimally invasive, i.e. urine or blood is collected. Fifth, since there may be a need to analyze archival samples, it is preferable that the biomarker is stable.

Thus, what is needed is a method of determining in vivo the ability of a test compound known or suspected to modulate Notch processing mediated by γ-secretase. As such, this invention demonstrates that TFF-3 can be used as a such a marker.

SUMMARY OF THE INVENTION

In one aspect, the present invention provides a method of identifying a modulator of Notch processing in vivo mediated by γ-secretase. In one embodiment, the method comprises (a) determining an amount of TFF-3 in a sample acquired from a query subject in the presence and absence of the test compound; and (b) comparing the amount of TFF-3 acquired from the query subject in the presence of the test compound with an amount of TFF-3 acquired from the query subject in the absence of the test compound; wherein a change in the amount of TFF-3 acquired in the presence of the test compound, compared with the amount of TFF-3 acquired in absence of the test compound, indicates the compound modulates Notch processing mediated by γ-secretase activity.

In one embodiment, the sample is feces, blood or plasma. The query subject can be selected from the group consisting of mice, rats, dogs, guinea pigs and humans.

In one embodiment, the step of determining the amount of TFF-3 can comprise determining an amount of mRNA encoding TFF-3 present in the sample. In another embodiment the step of determining the amount of TFF-3 comprises determining an amount of TFF-3 protein present in the sample. TFF-3 amounts can be determined by employing an analytical technique selected from the group consisting of Western blot, ELISA, RIA, quantitative real-time PCR, fluorescence activated cell sorting (FACs) and immunohistochemistry. The method can, but need not, be employed in a high-throughput operation. The method can further comprise repeating the method for each of a plurality of different test compounds. Additionally, the method can be performed in a clinical trial.

In another aspect, the present invention provides a method of identifying a preferred dose of a test compound known or suspected to modulate Notch processing in vivo mediated by γ-secretase. In one embodiment, the method comprises (a) determining an amount of TFF-3 in a sample acquired from a query subject in the absence of the test compound; (b) determining an amount of TFF-3 and a Notch-related toxicity level in a sample acquired from a query subject in the presence of a first dose of the compound; (c) repeating step (b) for a plurality of different test compound doses; (d) comparing (i) the TFF-3 amount; and (ii) the Notch-related toxicity acquired in the presence of two or more doses of the test compound; and (e) identifying a preferred dose of a compound known or suspected to modulate Notch processing mediated by γ-secretase based on an analysis of the comparison.

In one embodiment, the sample is feces, blood or plasma. The query subject can be selected from the group consisting of mice, rats, dogs, guinea pigs and humans.

In one embodiment, the step of determining the amount of TFF-3 can comprise determining an amount of mRNA encoding TFF-3 present in the sample. In another embodiment the step of determining the amount of TFF-3 comprises determining an amount of TFF-3 protein present in the sample. TFF-3 amounts can be determined by employing an analytical technique selected from the group consisting of Western blot, ELISA, RIA, quantitative real-time PCR, fluorescence activated cell sorting (FACs) and immunohistochemistry. The method can, but need not, be employed in a high-throughput operation. The method can further comprise repeating the method for each of a plurality of different test compounds. Additionally, the method can be performed in a clinical trial. The Notch-related toxicity can be, for example, gastrointestinal toxicity. The gastrointestinal toxicity can be, for example, goblet cell hyperplasia, crypt formation, crypt dilation and/or villus atrophy.

In yet another aspect, the present invention provides a method of generating a dosing schedule for a test compound known or suspected to modulate an activity mediated by γ-secretase. In one embodiment the method comprises (a) determining an amount of TFF-3 in a sample acquired from a query subject in the absence of the test compound; (b) determining an amount of TFF-3 in a sample acquired from the query subject in the presence of a first dose of the test compound at multiple time points; (c) repeating step (b) for one or more doses of the test compound (d) determining the Notch-related toxicity acquired in the presence of two or more doses of the test compound; and (e) generating a dosing schedule based on a comparison of the observed TFF-3 amounts and pharmacodynamics and associated Notch-related toxicity.

In one embodiment, the sample is feces, blood or plasma. The query subject can be selected from the group consisting of mice, rats, dogs, guinea pigs and humans.

In one embodiment, the step of determining the amount of TFF-3 can comprise determining an amount of mRNA encoding TFF-3 present in the sample. In another embodiment the step of determining the amount of TFF-3 comprises determining an amount of TFF-3 protein present in the sample. TFF-3 amounts can be determined by employing an analytical technique selected from the group consisting of Western blot, ELISA, RIA, quantitative real-time PCR, fluorescence activated cell sorting (FACs) and immunohistochemistry. The method can, but need not, be employed in a high-throughput operation. The method can further comprise repeating the method for each of a plurality of different test compounds. Additionally, the method can be performed in a clinical trial. The Notch-related toxicity can be, for example, gastrointestinal toxicity. The gastrointestinal toxicity can be, for example, goblet cell hyperplasia, crypt formation, crypt dilation and/or villus atrophy. The Notch-related toxicity can be determined by a technique selected from the group consisting of examining the immunohistochemistry of tissue sections and examining the morphology of goblet cells. The method can further comprising monitoring the dosing schedule.

DETAILED DESCRIPTION OF THE INVENTION

Figure 1:
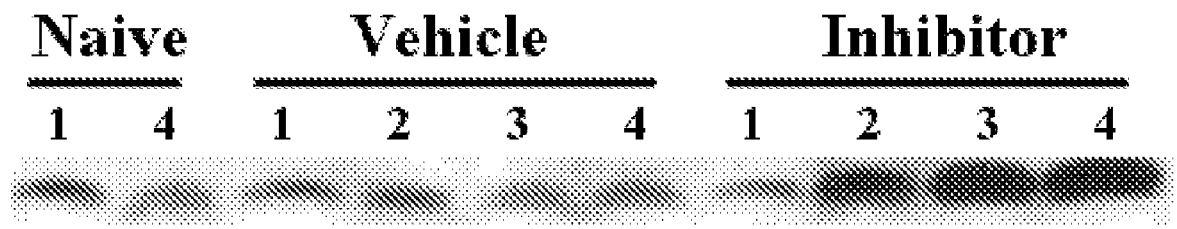
FIG. 1 represents an immunoblot which demonstrates the time dependent increase in TFF3 levels in fecal extracts in rats treated with the γ-secretase inhibitor. Animals were dosed with either vehicle or 1 mpk γ-secretase inhibitor QD for four days. Fecal pellets were collected over a 12 hr interval prior to dose 1 (1), dose 2 (2), dose 3(3) or dose 4 (4). Pellets were also collected from naive animals on day 1 and 4. Normalized fecal pellet extracts were separated by SDS-PAGE and analyzed for TFF3 protein by immunoblotting.

In one particular aspect of the present invention, TFF-3 was shown to be a biomarker for Notch-related toxicity. In another aspect, it is disclosed that TFF-3 is expressed in goblet cells and that TFF-3 levels can easily be detected using assays in feces, blood or plasma. TFF-3 can be detected in multiple species including rat, dog and human. As described herein, TFF-3 protein levels exhibit dose dependent reductions associated with γ-secretase inhibition. The changes observed for TFF-3 occur acutely following a single dose of compound and the changes observed correlate with the onset of Notch-mediated toxicity, particularly GI toxicity, which develops after 3 days of dosing. These results indicate that TFF-3 may be used as an acute predictive marker for monitoring and screening for Notch-related intestinal toxicity due to γ-secretase inhibition in both animal models and humans.

I. Definitions

Following long-standing patent law convention, the terms "a" and "an" mean "one or more" when used in this application, including the claims.

As used herein, the term "test compound" means any molecule, chemical entity, composition, drug, therapeutic agent, chemotherapeutic agent, or biological agent known or suspected to be capable of preventing, ameliorating, or treating a disease or other medical condition. The term includes small molecule compounds, antisense reagents, siRNA reagents, antibodies, and the like. A test compound can be assayed in accordance with the methods of the invention at any stage, e.g., during drug discovery or development, clinical trials, during pre-trial testing, or following FDA-approval.

As used herein, the term "about," when referring to a value or to an amount of mass, weight, time, volume, concentration or percentage is meant to encompass variations of ±20% or ±10%, more preferably ±5%, even more preferably ±1%, and still more preferably ±0.1% from the specified amount, as such variations are appropriate.

As used herein, the term "indicator" means any detectable substance that is known or suspected to be correlated with Notch processing mediated by γ-secretase. An indicator can take any chemical form and can be, for example, mRNA, a protein or protein fragment, a peptide, DNA or a small molecule.

As used herein, the term "Notch processing mediated by γ-secretase" means cleavage of one or more of the Notch family of proteins (1-4) at the S3 cleavage site by the γ-secretase complex.

As used herein, the term "Notch-related toxicity" means an undesired and/or deleterious effect that arises as a direct or indirect result of inhibition of Notch processing by γ-secretase. One example of Notch-related toxicity is GI toxicity. Another example of Notch-related toxicity is goblet cell hyperplasia.

As used herein, the term "high throughput" takes its ordinary meaning and refers to an operation in which a plurality of samples are run in a short period of time. For example, welled plates can be employed in a high throughput operation and can facilitate the rapid analysis of a plurality of samples.

II. Method Of Identifying a Test Compound That Modulates Notch Processing in Vivo Mediated by γ-Secretase Although γ-secretase modulators can be employed to combat AD, Notch-related toxicities have been observed in studies where animals have been dosed with γ-secretase inhibitors. Thus, when a γ-secretase modulator, or suspected modulator, is administered to a subject, the potential for effects on γ-secretase-mediated Notch-processing exists. In certain situations this could lead to Notch-related toxicities. It is desirable, therefore, to identify not only compounds that modulate an activity mediated by γ-secretase, but also to identify the degree of Notch-related toxicity, if any, associated with a given compound. This procedure can be employed in a range of applications, for example as a step in a compound screening process or as a component of a safety profile protocol. Ultimately, the procedure can lead to compounds that are effective γ-secretase modulators, yet also exhibit an acceptable Notch-related toxicity profile. Alternatively, modulation of γ-secretase-mediated Notch processing may itself be the therapeutic goal such as in the treatment of certain cancers. Although Notch processing can proceed by any of a variety of mechanisms, the present invention primarily addresses Notch processing mediated by γ-secretase.

In accordance with the above, in one embodiment of the present invention, a method of identifying a test compound that modulates Notch processing in vivo mediated by γ-secretase is disclosed. In one embodiment, the method comprises (a) determining an amount of TFF-3 in a sample acquired from a query subject in the presence and absence of a test compound; and (b) comparing the amount of TFF-3 acquired from the query subject in the presence of the test compound with the amount of TFF-3 acquired from the query subject in the absence of the test compound, wherein a change in the amount of TFF-3 acquired in the presence of the test compound, compared with the amount of TFF-3 acquired in absence of the test compound, indicates the compound modulates Notch processing mediated by γ-secretase activity.

A test compound employed in the method can be any compound that is known or suspected to modulate Notch processing mediated by γ-secretase. Such a test compound can comprise, but is not limited to, a small molecule. A test compound can also comprise, for example, a protein, which can comprise an antibody or a peptide, or a single or double-stranded nucleic acid such as DNA, RNA, an antisense reagent or an RNAi reagent.

Notch processing mediated by γ-secretase refers to cleavage of one or more of the Notch family of proteins at the S3 cleavage site by the γ-secretase complex.

In one step of the method, an amount of TFF-3 in a sample comprising feces, blood or plasma acquired from a query subject is determined in the presence and absence of the test compound. TFF-3 can be of any form; for example it may be mRNA or protein. In the present invention the term "amount" refers to a quantity of an indicator, and the measurement can be direct (e.g., a quantity of indicator) or indirect (e.g., a measure of fluorescence).

In this and other embodiments of the present invention, a sample can comprise feces, blood or plasma and is acquired from a query subject.

With further respect to a sample of the present invention, although a sample purification step can form an additional step in this and other embodiments of the present invention disclosed herein, such a purification step is optional. Indeed, one advantage of the present invention is that no sample preparation or purification is necessary.

In the present invention, a query subject can be any subject from which a sample can be obtained. For example, a query subject can be a human, rat, mouse, dog, or guinea pig.

The amount of TFF-3 is determined in the presence and absence of the test compound. The technique by which the determination is made is dependent, in part, on the nature of the TFF-3. In one example, when TFF-3 protein is measured, the determination can be made by quantitatively determining the amount of TFF-3 protein that is present in the sample. Standard molecular biological techniques can be employed in the quantitation of TFF-3 protein such as Western blot, ELISA, RIA, fluorescence activated cell sorting (FACS), immunohistochemistry and immunofluorescence microscopy. These standard analytical and biochemical techniques are well-known to those of ordinary skill in the art, and are described in various references (see, e.g., Sambrook et al., *Molecular Cloning: A Laboratory Manual.* $3^{rd}$ ed. Cold Spring Harbor Laboratory Press (2001) and Ausubel et al., *Short Protocols in Molecular Biology* (*Short Protocols in Molecular Biology*). $5^{th}$ ed. Wiley Publishers (2002), both of which are incorporated herein by reference).

In another example, mRNA encoding a TFF-3 protein can be an indicator; in this case, the determination can be made by quantitating the amount of mRNA encoding the protein that is present in the sample. Standard molecular biological techniques can be employed in the quantitation of mRNA such as quantitative real-time PCR (QRT-PCR) and Northern blotting. These standard analytical and biochemical techniques are well-known to those of ordinary skill in the art, and are described in various references (see, e.g., Sambrook et al., *Molecular Cloning: A Laboratory Manual.* $3^{rd}$ ed. Cold Spring Harbor Laboratory Press (2001) and Ausubel et al., *Short Protocols in Molecular Biolog* (*Short Protocols in Molecular Biology*). $5^{th}$ ed. Wiley Publishers (2002), both of which are incorporated herein by reference).

Continuing with the instant embodiment, once an amount of TFF-3 present in a sample is determined in the presence and absence of the test compound, the TFF-3 amount acquired from the query subject in the presence of the test compound is compared with a TFF-3 amount acquired from the query subject in the absence of the test compound. A change in the TFF-3 amount acquired in the presence of the test compound, compared with the TFF-3 amount acquired in absence of the test compound, indicates the compound modulates Notch processing mediated by γ-secretase activity.

The comparison can, but need not, comprise a statistical analysis of acquired data (e.g., TFF-3 amounts). A statistical analysis can provide additional information regarding the comparison, such as a confidence interval or margins of error.

The comparison indicates a degree to which a given compound modulates Notch processing mediated by γ-secretase is determined relative to a baseline, which is Notch processing determined in the absence of the test compound. This information can be particularly beneficial to screening protocols. Since the methods of the present invention do not require a sample purification step, although such a step can be performed and may sometimes be desirable, the methods are particularly amenable to inclusion in a high throughput screening process or system, although low throughput usage is also within the scope of the present invention. When the method forms a component of a high-throughput operation, welled plates, such as 96 well plates, can be employed.

When the method is employed in any screening operation, whether high or low throughput, the method can further comprise repeating the method for each of a plurality of different test compounds. In this application, the relative abilities of two or more test compounds in a sample set can be assayed to determine which one or more compounds of the sample set meet a given set of user-defined criteria; such criteria can include an identification of the test compound as the strongest modulator of Notch regulated γ-secretase activity in a panel of test compounds, the weakest modulator of Notch regulated γ-secretase activity in a panel of test compounds, or modulation of Notch regulated γ-secretase activity to a desired degree by a member of a panel of test compounds.

In the context of a screening operation, a user-selected activity cut-off value can be employed. In this context, test compounds exhibiting modulatory activity either above or below the cut-off can be pursued in additional studies, while those that do not meet this criteria are excluded from further characterization. In a further embodiment, the instant method can form a component of a clinical trial.

It is noted that although this embodiment of the present invention has been described in the context of identifying a modulator of Notch processing mediated by γ-secretase activity, the identification of test compounds that are not modulators can be equally valuable information and this forms yet another aspect of the invention.

III. Method of Identifying a Preferred Dose of a Test Compound Known or Suspected to Modulate Notch Processing in Vivo Mediated by γ-Secretase Under some conditions, modulation of Notch processing in vivo mediated by γ-secretase activity can result in Notch-related toxicity. More particularly, a given compound may be determined to be a highly effective modulator of γ-secretase activity, but such compounds can have unwanted side effects, including Notch-related toxicity due to inhibition of γ-secretase-mediated Notch processing. Until the present disclosure, those of ordinary skill in the art were unable to rapidly, accurately and conveniently determine the Notch-related toxicity associated with a given compound at a given dose unless such compounds were dosed for multiple days. The present invention solves this problem by providing a TFF-3 biomarker for assessing the level of γ-secretase-mediated Notch processing. The TFF-3 biomarker is predictive of Notch-related intestinal toxicity observed after multiple days of dosing. This ability can facilitate more efficient screening of γ-secretase modulators, with one benefit being the conservation of time and resources. The method offers the further advantage that a profile for a test compound can be generated that includes a measure of TFF-3 predictive of Notch-related toxicity. A preferred dose of a test compound can be determined to minimize the potential for Notch-related toxicity.

In some cases modulation of Notch processing mediated by γ-secretase may be the desired therapeutic goal. The present invention enables one to rapidly, accurately and conveniently determine compound efficacy by providing a biomarker for assessing the level of γ-secretase-mediated Notch processing.

One embodiment of a method of identifying a preferred dose of a test compound known or suspected to modulate Notch processing mediated by γ-secretase comprises determining an amount of TFF-3 in a sample acquired from a query subject in the absence of the test compound. As is the case with all the methods of the present invention, TFF-3 can be a protein, peptide or nucleic acid.

The step of determining an amount of TFF-3 in the sample will vary. For example, the determining can comprise determining an amount of mRNA encoding the TFF-3 that is present in the sample. In another example, when the TFF-3 is a protein, the determining can comprise determining an amount of TFF-3 protein is present in the sample. Standard molecular biological techniques can be employed in the quantitation of mRNA such as quantitative real-time PCR and Northern blotting. Standard molecular biological techniques can be employed in the quantitation of a TFF-3 protein such as Western blot, ELISA, RIA, fluorescence activated cell sorting (FACS), immunohistochemistry, quantitative RT-PCR (QRT-PCR) and immunofluorescence microscopy. These standard analytical and biochemical techniques are well-known to those of ordinary skill in the art, and are described in various references (see, e.g., Sambrook et al., *Molecular Cloning: A Laboratory Manual*. 3$^{rd}$ ed. Cold Spring Harbor Laboratory Press (2001) and Ausubel et al., *Short Protocols in Molecular Biology* (*Short Protocols in Molecular Biology*). 5$^{th}$ ed. Wiley Publishers (2002), both of which are incorporated herein by reference).

The method can further comprise an optional sample purification step, such as the isolation from feces, blood or plasma, although no such a purification step is necessary.

A sample of the present invention is acquired from a query subject, which can be any subject from which a sample can be obtained. Examples of a sample include feces, blood or plasma. Representative examples of query subjects of the present invention include humans, rats, mice, dogs, or guinea pigs.

After the sample is acquired the amount of TFF-3 is determined to establish a baseline. Query subjects are then dosed with a test compound at different doses. A second sample is then acquired and the amount of TFF-3 determined. The change in the amount of TFF-3 observed between the first and second sample measures the change in γ-secretase-mediated Notch processing. Where appropriate, a measure of Notch-related toxicity, including but not limited to alterations in gastrointestinal differentiation, can be determined in subjects dosed with test compounds for multiple days. Alterations in gastrointestinal differentiation can be assessed by examining tissue sections by immunohistochemical techniques for goblet cell hyperplasia, crypt formation, crypt dilation and/or villus atrophy.

The Notch-related toxicity associated with a particular test compound at a particular dose can be quantitatively determined to facilitate a numerical comparison with results obtained from other test compounds and/or doses. For example, a scoring scale can be employed to assign numerical values to the amount of Notch-related toxicity that is observed for a given test compound at a given dose.

Alternatively, a qualitative assessment of Notch-related toxicity can be made. Notch-related toxicity, in the context of the present invention, includes, but is not limited to gastrointestinal toxicity. In this approach, tissue sections can be examined for goblet cell hyperplasia and an overall assessment of deviations from a predetermined set of criteria taken as baseline (e.g., "normal") noted in a non-numerical format, such as a description of the nature, degree, indications and/or extent of deviations from baseline. For example, general descriptions such as "minimal changes in morphology observed" or "significant changes in morphology observed" can be employed (e.g., Table 1).

Continuing with this embodiment of the method, the above steps can be repeated for a plurality of different test compound doses. By repeating the steps at different test compound doses, a database of TFF-3 amounts and Notch-related toxicities can be compiled for a range of different test compound doses to establish a correlation between the TFF-3 and Notch-related toxicities.

After acquiring data comprising TFF-3 amounts and Notch-related toxicities at different doses, the TFF-3 amounts and Notch-related toxicities acquired in the presence of two or more doses of the test compound are compared. The comparison can take any form and can depend on the nature of the Notch-related toxicity data that is being employed. By way of example, if a quantitative measure of Notch-related toxicity is employed, the toxicities can be numerically compared. If a qualitative measure is being employed, general descriptors can be compared. The results of the comparison can be used to establish the relationship between the level of the TFF-3 and any Notch-related toxicity observed after two or more doses.

Finally, a preferred dose of a compound known or suspected to modulate Notch processing mediated by γ-secretase activity can be identified based on an evaluation of the amount of TFF-3 observed at a given dose of a test compound. In such an analysis, doses at which higher changes in TFF-3 are observed may be excluded as less preferred, due to the risk of Notch-related toxicities in a test subject or patient. Similarly, doses at which only small changes in TFF-3 are observed may be preferable to minimize the risk for Notch-related toxicities.

In a related application of the present invention, the described methods can be employed to evaluate each of a plurality of different test compounds. This application can form an element of an overall screening operation or as an element of a protocol for optimizing a particular modulator of an activity mediated by γ-secretase. The method can be employed in a clinical or pre-clinical (e.g., drug discovery) setting.

IV. Method of Generating a Dosing Schedule for a Test Compound Known or Suspected to Modulate an Activity Mediated by γ-Secretase In some situations, it can be desirable to generate a dosing schedule for a modulator. In the context of the present invention, a dosing schedule can be generated in which the potential for developing a Notch-related toxicity is monitored using TFF-3 as a function of time. This type of dosing schedule can provide guidelines as to when, and how much of, a preferred dose of a test compound, which can be identified as described above, should be administered to a patient. By following a dosing schedule generated as described herein, a physician or researcher administering the test compound can minimize unwanted toxic effects due to Notch-related toxicity.

Accordingly, in yet a further embodiment of the present invention, a method of generating a dosing schedule for a test compound known or suspected to modulate an activity mediated by γ-secretase is provided. In one embodiment of the method, the TFF-3 level in a sample is acquired from a query subject in the absence of a test compound.

Continuing, the TFF-3 amount in a sample comprising feces, blood or plasma acquired from the query subject in the presence of a first dose of the test compound at a first time point is determined. The step of determining an amount of TFF-3 in the sample will depend on the nature of the indicator. For example, the determining can comprise determining an amount of mRNA encoding TFF-3 that is present in the sample. In another example, when the TFF-3 is a protein, the determining can comprise determining an amount of TFF-3 protein that is present in the sample. Standard molecular biological techniques can be employed in the quantitation of mRNA such as quantitative real-time PCR and Northern blotting. Standard molecular biological techniques can be employed in the quantitation of TFF-3 protein such as Western blot, ELISA, RIA, fluorescence activated cell sorting (FACS), immunohistochemistry, quantitative RT-PCR (QRT-PCR) and immunofluorescence microscopy. These standard analytical and biochemical techniques are well-known to those of ordinary skill in the art, and are described in various references (see, e.g., Sambrook et al., *Molecular Cloning: A Laboratory Manual*. $3^{rd}$ ed. Cold Spring Harbor Laboratory Press (2001) and Ausubel et al., *Short Protocols in Molecular Biology* (*Short Protocols in Molecular Biology*). $5^{th}$ ed. Wiley Publishers (2002), both of which are incorporated herein by reference).

In the instant method, a representative sample comprises, for example, feces, blood or plasma acquired from a query subject. As stated herein, no sample preparation is necessary, although in some cases one or more sample preparation and/or purification steps may be desirable.

An amount of TFF-3 in a sample comprising feces, blood or plasma acquired from the query subject in the presence of a first dose of the test compound at a first time point is then determined. The first dose can be selected based on a previous assessment of the efficacy of the test compound. After administering a first dose, the sample can be acquired at a first time point. As is the case with the first dose of the test compound, the first time point can be selected based on prior studies of the test compound. The technique employed for the determining can follow the guidelines described herein, and will depend, in part, on the nature of the indicator.

Continuing, Notch-related toxicity including, but not limited to, alterations in gastrointestinal differentiation can be determined in subjects dosed with test compounds for multiple days. Alterations in gastrointestinal differentiation can be assessed by examining tissue sections by immunohistochemical techniques for goblet cell hyperplasia, crypt formation, crypt dilation and/or villus atrophy.

The steps of determining TFF-3 amounts at multiple time points following a dose and determining Notch-related toxicity can then be performed for two or more different doses of the test compound. This step can be repeated for any number of test compound doses. By repeating the process at different test compound doses, a database of Notch-related toxicities for different doses and different pharmacokinetic profiles can be compiled.

Finally, a dosing schedule based on the observed TFF-3 amount and Notch-related toxicity associated with a dose and a pharmacokinetic profile of the test compound can be generated. A dosing schedule will take into account Notch-related toxicities associated with different test compound doses and pharmacokinetic profiles. Together, this information can provide a researcher with a profile of a compound's activity at different time points, which can be used to optimize a treatment regimen for a patient.

This embodiment of the present invention can be employed in a high-throughput operation and, in one embodiment of the method, the method can be repeated for each of a plurality of different test compounds. When the method forms a component of a high-throughput operation, welled plates, such as 96 well plates, can be employed.

This embodiment can be performed in a clinical trial. In one aspect of this embodiment, the method further comprises monitoring the dosing schedule so as to minimize toxicity yet maximize an efficacious treatment regimen.

In all embodiments of the present invention, a test compound can be administered using any suitable drug delivery technique known in the art, such as orally or parenterally. The selection of a delivery technique will be a function of the physical and chemical properties of the test compound itself and, consequently, the formulation can dictate appropriate routes of delivery. In one embodiment, a test compound is formulated in accordance with routine procedures as a pharmaceutical composition adapted for intravenous administration to human beings. Typically, test compounds for intravenous administration are solutions in sterile isotonic aqueous buffer. Where necessary, a test compound may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a test compound is to be administered by infusion, it can be dispensed with an infusion bottle containing sterile pharmaceutical grade water or saline. Where a composition is administered by injection, an ampoule of sterile water for injection or saline can be provided so that the ingredients may be mixed prior to administration.

V. Method of Inhibiting TFF-3 Activity

In some situations, it can be desirable to utilize an antagonist of TFF-3 in order to prevent or treat γ-secretase inhibitor induced toxicity. In the context of the present invention, any molecule that alters TFF-3 cellular effects is a candidate antagonist. Screening techniques well known to those skilled in the art can identify these molecules. Examples of antagonists include but are not limited to: (1) small organic and inorganic compounds, (2) small peptides, (3) antibodies and derivatives, (4) polypeptides closely related to TFF-3, (5) antisense DNA and RNA, (6) ribozymes, (7) siRNA, (8) triple DNA helices and (9) nucleic acid aptamers.

Small molecules that bind to a relevant part of the TFF-3 polypeptide and inhibit the biological activity of TFF-3 are also antagonists. Examples of small molecule antagonists include small peptides, peptide-like molecules, preferably soluble, and synthetic non-peptidyl organic or inorganic compounds.

Antisense RNA or DNA constructs can be effective antagonists. Antisense RNA or DNA molecules block function by inhibiting translation by hybridizing to targeted mRNA. Antisense technology can be used to control gene expression through triple-helix formation or antisense DNA or RNA, both of which depend on polynucleotide binding to DNA or RNA. For example, the 5' coding portion of a TFF-3 sequence is used to design an antisense RNA oligonucleotide of from about 10 to 40 base pairs in length. A DNA oligonucleotide is designed to be complementary to a region of the gene involved in transcription (triple helix) (Beal and Dervan, 1991; Cooney et al., 1988; Lee et al., 1979), thereby preventing transcription and the production of TFF-3. The antisense RNA oligonucleotide hybridizes to the mRNA in vivo and blocks translation of the mRNA molecule into TFF-3 (antisense) (Cohen, 1989; Okano et al., 1991). These oligonucleotides can also be delivered to cells such that the antisense RNA or DNA may be expressed in vivo to inhibit production of TFF-3. When antisense DNA is used, oligodeoxyribonucleotides derived from the translation-initiation site, e.g., between about −10 and +10 positions of the target gene nucleotide sequence, are preferred.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques (WO 97/33551, 1997; Rossi, 1994).

To inhibit transcription, triple-helix nucleic acids that are single-stranded and comprise deoxynucleotides are also useful antagonists. These oligonucleotides are designed such that triple-helix formation via Hoogsteen base-pairing rules is promoted, generally requiring stretches of purines or pyrimidines (WO 97/33551, 1997).

Aptamers are short oligonucleotide sequences that can be used to recognize and specifically bind almost any molecule. The systematic evolution of ligands by exponential enrichment (SELEX) process (Ausubel et al., 1987; Ellington and Szostak, 1990; Tuerk and Gold, 1990) is powerful and can be used to find such aptamers. Aptamers have many diagnostic and clinical uses; almost any use in which an antibody has been used clinically or diagnostically, aptamers too may be used. In addition, they are cheaper to make once they have been identified, and can be easily applied in a variety of formats, including administration in pharmaceutical compositions, in bioassays, and diagnostic tests (Jayasena, 1999).

EXAMPLES

The following Examples have been included to illustrate various exemplary modes of the invention. Certain aspects of the following Examples are described in terms of techniques and procedures found or contemplated by the inventors to work well in the practice of the invention. These Examples are exemplified through the use of standard laboratory practices of the inventors. In light of the present disclosure and the general level of skill in the art, those of skill will appreciate that the following Examples are intended to be exemplary only and that numerous changes, modifications and alterations can be employed without departing from the spirit and scope of the invention.

Example 1

Dose Dependent Increase in TFF-3 expression in the Duodenum after Treatment with a γ-Secretase Inhibitor Duodenal rat tissue sections were immunostained for TFF-3 expression after treatment with a γ-secretase inhibitor. The results show that TFF-3 protein expression increase in response to γ-secretase inhibition.

Rats were treated with the γ-secretase inhibitor BMS-573100 for 3 days and then the duodenum was removed, embedded in paraffin and cut into 5 μm sections. The sections were then deparaffinized by heating at 58° C. for 20 min, and then rinsing them in xylene three times for five minutes each rinse. The sections were then rehydrated through a series of washes comprising 100% ethanol for 5 min, 90% ethanol for 5 min, 80% ethanol for 5 min, water for 5 min and PBS for 5 min. Heat induced epitope retrieval (HIER) was then performed whereby the sections were boiled for 10 min in a 10 mM Tris/1 mM EDTA buffer, pH 9.0. The sections were then cooled to room temperature for 25 min and then rinsed in water twice and rinsed in PBS twice. The sections were then blocked with 5% bovine serum albumin (BSA) in PBS for 30 min at room temperature, incubated with a goat anti-mouse TFF-3 antibody (Santa Cruz, Calif.) for 1 hr at room temperature and then rinsed three times in PBS for 3 min each rinse. The sections were then incubated with a rabbit anti-goat Alexa-Fluor 594 secondary antibody (Invitrogen/Molecular Probes, Carlsbad, Calif.) for 1 hr at room temperature and then rinsed three times in PBS for 3 min each rinse. The sections were then stained with 4', 6-Diamidino-2-phenylindole (DAPI, Molecular Probes) for 1 min and then washed and mounted in antifade solution. Fluorescence microscopy was performed using a 300 nM light source.

These results demonstrate that TFF-3 expression is markedly increased in the duodenal sections treated with the γ-secretase inhibitor for three days as compared to those that were not treated (Data not shown). Further, TFF-3 expression increases in a dose dependent fashion with the amount of γ-secretase administered.

Example 2

TFF3 Levels Increase in Fecal Extracts after each Dosage of Treatment with with a γ-Secretase Inhibitor An immunoblot was prepared which examined TFF-3 protein expression over time after treatment with a γ-secretase inhibitor.

Fecal extracts were prepared from 3 rat fecal pellets using 1.5 ml RIPA buffer (150 mM NaCl, 1% Triton x-100, 0.5% Na Deoxycholate, 0.1% SDS, 50 mM Tris pH 8.0 and 1× Roche protease inhibitor cocktail) with mechanical homogenization followed by spinning at 5000×g to remove insoluble material. Total protein concentration was determined using a BCA assay (Biorad) and equal protein was run on a 4-12% bis-tris Nu-Page mini-gel (Invitrogen, Carlsbad, Calif.) and transferred to nitrocellulose according to the manufacturer's protocol. Immunoblots were blocked for 1.5 hrs in 5% milk/1× XPBS +0.05% Tween-20 at 40C, then probed overnight at 4° C. with an Anti-ITF(A-20) goat polyclonal affinity purified antibody (Santa Cruz Biotechnology) at a 1:500 dilution in 5% milk/1× PBS. Immunoblots were washed with 1× PBS +0.1% Tween-20 followed by probing with an anti-goat HRP antibody (Jackson Immunosearch Labs) at a 1:5000 dilution for 1 hour at room temperature in 5% milk/1× PBS. The immunoblots were then washed with 1×PBS/0.1% Tween-20 and developed using West Dura Substrate (Pierce) according to the manufacturer's directions followed by exposure to film.

As shown in FIG. 1, with each consecutive dosage of treatment with a γ-secretase treatment over a 12 hr period, TFF-3 protein expression increases compared to the vehicle controls. These results indicate that TFF-3 is a suitable biomarker for intestinal toxicity following treatment with a γ-secretase inhibitor.

Example 3

Correlation of Plasma TFF-3 Protein Levels and Gastrointestinal Toxicity in Dogs Following Treatment with Various γ-Secretase Inhibitors The level of TFF-3 protein in the plasma was measured in dogs after treatment with three different γ-secretase inhibitors which showed both a dose dependent and time dependent increase in TFF-3 expression.

The results demonstrate that TFF-3 expression increases in the plasma after treatment with a γ-secretase inhibitor as shown in Table 1. The results further indicate that as TFF-3 expression increases, the pathology of the gastrointestinal tract worsens, for example, with an increase in goblet cells, cryptic cysts and villus atrophy. The level of hyperplasia observed is indicated in Table 1 by a toxicity score ranked on a scale of 2-5 with 5 being the most affected. NAD=no adverse effects detected. 2-5× increases in plasma TFF-3 levels are observed on days 3 and 4 in animals exhibiting the GI lesion. Also, TFF-3 levels increased in response to three different γ-secretase inhibitors thereby confirming that the results are reliable and that TFF-3 has therapeutic value as a biomarker of intestinal toxicity.

TABLE 1

|  | Animal # | Pre-Dose TFF3 (pg/ml) | Plasma TFF3 (% of Pre-Dose) | | | Duodenal Tox Observation |
|---|---|---|---|---|---|---|
|  |  |  | Day 1 | Day 3 | Day 4 |  |
| Vehicle | 1 | 2381 | 70 | 92 | 104 | NAD |
|  | 2 | 1794 | 76 | 122 | 104 | NAD |
| Compound 1 10 mpk | 1 | 1468 | 112 | 148 | 207 | ↑ goblet cells (3) |
|  | 2 | 1603 | 94 | ND | 276 | ↑ goblet cells (3) |
| Compound 1 20 mpk | 1 | 1652 | 121 | 355 | 405 | ↑ goblet cells, cystic crypts, villus atrophy (4-5) |
|  | 2 | 1247 | 191 | 528 | 495 | ↑ goblet cells, cystic crypts, villus atrophy (4-5) |
| Compound 2 10 mpk | 1 | 1340 | 86 | 163 | 120 | minimal ↑ goblet cells (2-5) |
|  | 2 | 1486 | 88 | 192 | 264 | moderate ↑ goblet cells (3) |
| Compound 2 20 mpk | 1 | 1630 | ND | 246 | 475 | ↑ goblet cells, cystic crypts, villus atrophy (4-5) |
|  | 2 | 2437 | 91 | 242 | 291 | moderate ↑ goblet cells (3), some crypt dialation |
| Compound 3 10 mpk | 1 | 1789 | 102 | 130 | 126 | minimal ↑ goblet cells (2-5) |
|  | 2 | 1192 | ND | 157 | 165 | minimal ↑ goblet cells (2-5) |

†Rat duodenal scoring system is a scale from 2-5: 2 = normal, 3 = mild goblet cell metaplasia; 4 = moderate goblet cell metaplasia, marked villous atrophy, cystic crypts; 5 = marked goblet cell metaplasia, significant villous atrophy, occasionally with mononuclear infiltrate.

Beagle dogs were dosed with γ-secretase inhibitors by mouth (PO), every day (QD) for 4 days. Plasma TFF-3 levels were measured by dog TFF3 ELISA in blood samples collected predose and at 5 hr post dose on day 1, day 3 and day 4 (termination) and compared to predose controls levels. Plasma TFF3 signal specificity was verified by immunodepletion and spike and recovery experiments. Goblet cell hyperplasia was assessed in duodenum tissue by periodic acid Schiff (PAS) staining.

Figure 2:
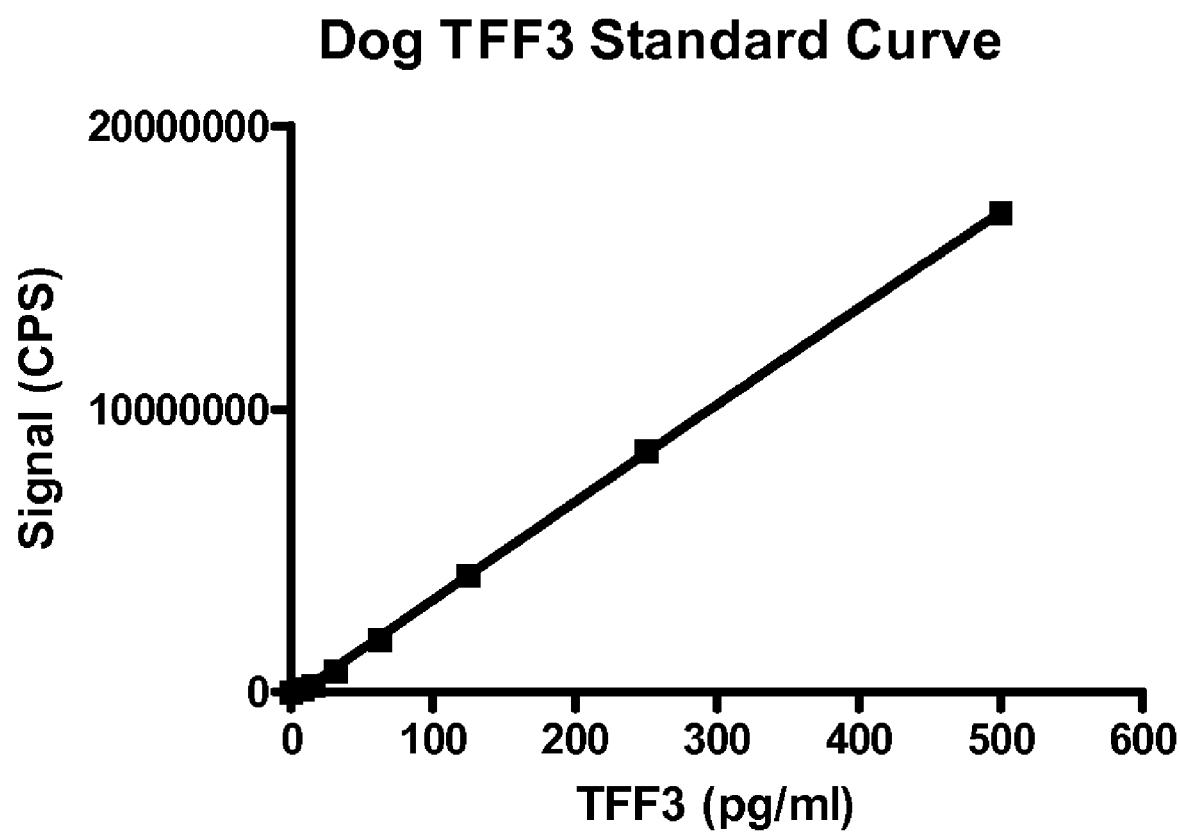
FIG. 2 represents an exemplary standard curve using purified dog TFF-3.

For the ELISA, dog TFF-3 expressed in E. coli was purified and used to immunize rabbits. Rabbit polyclonal antisera was affinity purified on a TFF-3 affinity column. Anit-TFF-3 polyclonal antibodies from two different immunized rabbits were used to generate a TFF-3 ELISA assay. An example standard curve using purified dog TFF-3 is shown in FIG. 2. The assay sensitivity is 2-4 pg/ml.

Beagle dogs were dosed PO, QD with γ-secretase inhibitors for 4 days. Plasma TFF3 levels were measured by dog TFF3 ELSIA in blood samples collected predose and at 5 hr post dose on day 1, day 3 and day 4 (termination) and are expressed relative to predose controls levels. Plasma TFF3 signal specificity was verified by immunodepletion and spike and recovery experiments. Goblet cell hyperplasia was assessed in duodenum tissue by PAS staining; the level of hyperplasia observed is indicated by a toxicity score ranked on a scale of 2-5 with 5 being the most affected. NAD=no adverse effects detected. 2-5× increases in plasma TFF3 levels are observed on days 3 and 4 in animals exhibiting the GI lesion.

REFERENCES

The references cited in the specification are incorporated herein by reference to the extent that they supplement, explain, provide a background for or teach methodology, techniques and/or compositions employed herein. All publications and patents, including patent applications, referred to in this application are herein expressly incorporated by reference.

It will be understood that various details of the invention may be changed without departing from the scope of the invention. Furthermore, the foregoing description is for the purpose of illustration only.

The invention claimed is:

1. A method of identifying a modulator of Notch processing in vivo mediated by γ-secretase comprising:
    (a) determining a first amount of Trefoil factor-3 (TFF-3) in a sample acquired from a query subject;
    (b) administering a test compound to the query subject wherein the test compound is a known γ-secretase modulator or a suspected γ-secretase modulator;
    (c) determining a second amount of TFF-3 in a sample acquired from the query subject after administration of the test compound; and
    (d) comparing the first amount of TFF-3 acquired from the query subject to the second amount of TFF-3 acquired from the query subject after administration of the test compound;
wherein a change in the amount of TFF-3 acquired after administration of the test compound, compared with the amount of TFF-3 acquired before administration of the test compound, indicates the compound modulates Notch processing mediated by γ-secretase activity.

2. The method of claim 1, where the query subject is selected from the group consisting of mice, rats, dogs, guinea pigs and humans.

3. The method of claim 1, wherein the step of determining the amount of the TFF-3 is selected from the group consisting of determining an amount of mRNA encoding the TFF-3 protein present in the sample and determining an amount of TFF-3 protein present in the sample.

4. The method of claim 1, wherein the first and second TFF-3 amounts acquired from the query subject are determined by employing an analytical technique selected from the group consisting of Western blot, ELISA, RIA, quantitative real-time PCR, fluorescence activated cell sorting (FACs) and immunohistochemistry.

5. The method of claim 1, wherein the step of comparing the first and second amounts of TFF-3 acquired from the query subject is employed in a high-throughput operation.

6. The method of claim 1, further comprising repeating the method for each of a plurality of different test compounds.

7. The method of claim 1, wherein the method is performed in a clinical trial.

* * * * *

UNITED STATES PATENT AND TRADEMARK OFFICE
CERTIFICATE OF CORRECTION

PATENT NO. : 7,601,540 B2
APPLICATION NO. : 11/779306
DATED : October 13, 2009
INVENTOR(S) : Denton et al.

It is certified that error appears in the above-identified patent and that said Letters Patent is hereby corrected as shown below:

First Page Column 2
Line 16, "exhibitearlyembryonic" should read -- exhibit early embryonic --.

Column 18
Line 16, "(FACs)" should read -- (FACS) --.

Signed and Sealed this

Twenty-ninth Day of December, 2009

David J. Kappos
*Director of the United States Patent and Trademark Office*